United States Patent
Wilson et al.

(10) Patent No.: US 7,361,374 B2
(45) Date of Patent: Apr. 22, 2008

(54) APPLICATION FOR HOP ACIDS AS ANTI-MICROBIAL AGENTS

(75) Inventors: Richard J. H. Wilson, Copthorne (GB); Robert J. Smith, Yakima, WA (US); Gerhard Haas, Woodcliff Lake, NJ (US)

(73) Assignee: S.S. Steiner, Inc., New York, NY (US)

( * ) Notice: Subject to any disclaimer, the term of this patent is extended or adjusted under 35 U.S.C. 154(b) by 295 days.

(21) Appl. No.: 10/438,656

(22) Filed: May 15, 2003

(65) Prior Publication Data

US 2003/0215535 A1 Nov. 20, 2003

Related U.S. Application Data

(60) Provisional application No. 60/381,659, filed on May 17, 2002.

(51) Int. Cl.
*A61K 36/00* (2006.01)

(52) U.S. Cl. .................... 424/778; 424/725

(58) Field of Classification Search ............... 424/778, 424/725
See application file for complete search history.

(56) References Cited

U.S. PATENT DOCUMENTS

| | | | |
|---|---|---|---|
| 3,486,906 A | 12/1969 | Todd et al. ............ 99/50.5 |
| 4,340,763 A * | 7/1982 | Wuesthoff ............. 568/344 |
| 5,166,449 A | 11/1992 | Todd, Jr. et al. ........ 568/377 |
| 5,286,506 A | 2/1994 | Millis et al. ............ 426/335 |
| 5,370,863 A | 12/1994 | Barney et al. ........... 424/49 |
| 5,455,038 A | 10/1995 | Barney et al. ........... 424/405 |
| 5,583,262 A | 12/1996 | Maye et al. ............. 568/377 |
| 5,624,701 A * | 4/1997 | Maye et al. ............. 426/600 |
| 6,083,254 A | 7/2000 | Evans .................... 607/96 |
| 6,251,461 B1 * | 6/2001 | Johnson et al. ......... 426/335 |
| 6,352,726 B1 | 3/2002 | Haas et al. ............. 424/725 |
| 6,379,720 B1 | 4/2002 | Cooper et al. .......... 424/778 |
| 6,386,144 B1 | 5/2002 | Cathey .................. 119/172 |
| 6,423,317 B1 | 7/2002 | Haas et al. ............. 424/195.18 |
| 6,451,365 B1 | 9/2002 | King et al. ............. 426/326 |
| 6,475,537 B1 | 11/2002 | King et al. ............. 424/778 |
| 6,893,857 B1 | 5/2005 | Maye et al. ............. 435/243 |
| 2002/0197366 A1 | 12/2002 | King et al. ............. 426/335 |
| 2003/0013773 A1 | 1/2003 | Haas ..................... 514/690 |
| 2004/0131709 A1 | 7/2004 | Berdahl et al. ......... 424/745 |
| 2004/0175480 A1 | 9/2004 | Seman et al. ........... 426/600 |

FOREIGN PATENT DOCUMENTS

| | | |
|---|---|---|
| CN | 1450864 | 10/2003 |
| EP | 0 681 029 | 4/1995 |
| GB | 1112795 | 2/1966 |
| WO | WO 97/33971 | 9/1997 |
| WO | WO 00/52212 | 9/2000 |
| WO | WO 01/06877 | 1/2001 |
| WO | WO 02/078450 | 10/2002 |

OTHER PUBLICATIONS

"Factors Affecting Antibacterial Activity of Hop Compounds and Their Derivatives" Simpson et al,. *Journal of Applied Bacteriology*, 1992, 72, 327-334.

"Membrane Leakage in *Bacillus subtills* 168 Induced by the Hop Constituents Lupulone, Humulone, Isohumulone and Humulinic Acid" Teuber et al., *Arch Mikrobiol*. 94, 1973, 159-171.

Kalsec Product Brochure, KAE LNB HOP Extract Blend, Product Code 46-51, Kalsec, Inc., Oct. 1994.

* cited by examiner

*Primary Examiner*—Christopher R Tate
*Assistant Examiner*—Randall Winston
(74) *Attorney, Agent, or Firm*—Hayes Soloway P.C.

(57) ABSTRACT

The alkali metal salts form of β-acids dissolved in propylene glycol is used to control microbial growth in food products, process streams and other applications, including in cosmetic formulations.

7 Claims, 1 Drawing Sheet

US 7,361,374 B2

APPLICATION FOR HOP ACIDS AS ANTI-MICROBIAL AGENTS

CROSS-REFERENCE TO RELATED APPLICATION

This Application claims priority from U.S. Provisional Application No. 60/381,659, filed May 17, 2002.

FIELD OF THE INVENTION

The present invention relates to the use of hop-derived β-acids extracts in propylene glycol for controlling bacterial growth. The invention has particular utility in connection with control of bacteria in raw foods processing industries, such as sugar processing and poultry processing industries, and also has application in cosmetics and pharmaceuticals although other utilities are contemplated.

BACKGROUND OF THE INVENTION

Hops are primarily used in the brewing of beer. It is known that compounds derived from flowers of the female hop plant (*Humulus lupulus L.*) contribute a desirable bitter flavor to beer. This bitterness derives from the so-called α-acids, an homologous series of organic acids that are converted during the boiling of the brewer's wort into highly bitter, isomerized α-acids (iso-α-acids). Hops also contain an analogous series of β-acids. These substances, which have very low aqueous solubility, are of little value in brewing and are almost entirely eliminated from the wort by precipitation in the proteinaceous "trub" that forms during the boil. Many brewers now use extracts of hops which are convenient and much more stable that the traditional dried hops. Such products are made by extracting the hops with organic solvent (almost exclusively ethanol) or, more commonly, with carbon dioxide in either liquid or supercritical state. These extracts contain high contents of α-acids and β-acids, most of the remainder consisting of hop oils, waxes and uncharacterized resins. Typically, the α-acids content of a hop extract is in the range 35–65% by weight, that of the β-acids 15–40%. Hop processing companies have for many years also offered brewers a choice of more refined products that are prepared from the hop extracts by means of fractionation and chemical conversion, many of which may be added into the brewing process after fermentation of the wort. Such products include aqueous preparations of purified iso-α-acids, and their chemically reduced derivatives, especially tetrahydroiso-α-acids. In the course of preparation of these products, the hop processor will typically obtain a by-product fraction that comprises primarily a mixture of β-acids and hop oils, plus some minor components including waxes and small amounts of iso-α-acids. This fraction, commonly known as "β-Fraction" "Beta Aroma Extract" or "Base Extract" is often sold to brewers for addition to the wort kettle, where the hop oil component imparts aromatic flavors. However, it is also common to separate the oils from the β-acids, enabling a more potent "Aroma Extract" to be offered and releasing the β-acids for other uses.

In addition to being used for the purpose of contributing bitter and aromatic flavors to beer, hops are known to be useful to control bacterial growth during the brewing process. It has been demonstrated that the hop resin acids (α-acids, β-acids, iso-α-acids and chemically reduced iso-α-acids such as tetrahydroiso-α-acids) have anti-microbial activity and are especially active against Gram positive bacteria. Consequently, several uses for hop resin acids in food processing, cosmetic and pharmaceutical applications have been described. β-acids are generally considered to be particularly effective, natural agents. In WO 00/52212 it is noted that "certain hop acids exhibit anti-bacterial effects in sugar containing aqueous mediums. For example, European Patent Application No. 681 029 A2 discloses a process for inhibiting thermophilic micro-organisms in the presence of sucrose aqueous medium, in which a hop based product is added to a sucrose aqueous medium at temperatures between 50° C. and 80° C. And, U.S. Pat. No. 5,286,506 discloses a process of applying a solution containing beta acids to a solid food product to prevent growth of Listeria. According to Arch. Mikrobiol. 94 (1973), p. 159–171 beta acids exhibit the highest bacteriostatic effect in comparison to alpha acids and isoalpha acids; however, because of its poor solubility, certain concentrations of beta-acids cannot be exceeded." Hop resin acids, especially β-acids, have also been claimed as effective antibacterial agents in food processing in US Publication No. 2002/0197366, U.S. Pat. No. 6,251,461 and U.S. Pat. No. 6,475,537, and have recently also been shown to have useful activity against algal growth in water systems (U.S. Pat. No. 6,379,720 and PCT Application No. WO 02/078450), protozoa (U.S. Pat. No. 6,352,726 and U.S. Pat. No. 6,423,317) and have been proposed as active agents against mastitis in cows, wherein the hop compound can be applied to the udders and teats of cows (US Patent Application Ser. No. 2003/0013773. The possibility to use hop acids in mouthwashes or toothpastes to suppress the activity of *Streptococcus mutans* and thus help to prevent caries has been described in U.S. Pat. No. 5,370,863. The general mechanism by which hop acids are believed to act against susceptible (Gram +ve) bacteria has been discussed by Simpson and Smith (Simpson, W. J., and Smith, A. R. W., 1992 in "Factors affecting antimicrobial activity of hop compounds and their derivatives". The Journal of Applied Bacteriology 72 (4):327–334).

Because most agricultural products come from the field, bacterial contamination is unavoidable. Similarly, bacterial contamination of fresh meats is difficult to avoid.

Recently, the beet sugar industry has begun to use β-acids at a few ppm level as an agent for controlling bacterial growth in beet sugar processing. More particularly, the sugar industry has used β-acids in aqueous, alkaline solution as an additive during processing of sugar beets. However, since β-acids preparations are usually somewhat bitter (probably in the most part due to contamination with small amounts of the highly bitter iso-α-acids), they are used quite sparingly. WO 00/52212 teaches that an aqueous, alkaline solution of β-acids can be prepared at a concentration of about 10% by weight and that in this form the antibacterial activity is better than that of a similar quantity of β-acids applied as an emulsion or dissolved in organic solvent. However, a considerable practical disadvantage of such solutions is their tendency during storage to precipitate waxy or resinous matter that may foul pipelines and dosing pumps. The solutions must also be kept from freezing and so may require heating during transport and storage in cold times of the year. However, such solutions are relatively unstable. In contrast, we find that β-acids, when dissolved into propylene glycol in the form of their alkali metal salts, have chemical and physical stability over a wide temperature range and may be prepared at substantially and usefully higher concentrations. The use of propylene glycol as a solvent for many organic substances is well-known, and it has also been used as an aid to the solubilisation of isomerized and chemically reduced, isomerized α-acids. For example, Paul Todd, Jr. in U.S. Pat. No. 3,486,906 describes the preparation of iso-α-acids dissolved in their free acid form.

SUMMARY OF THE INVENTION

The present invention discloses that certain hops extracts, namely β-acids in alkali metal salt form are soluble and stable when dissolved in propylene glycol (1,1-propanediol), and are therefore especially useful as antibacterial agents for treatment of a wide variety of food products, including addition to sugar-rich liquid process streams such as occur in the sugar processing and distilling industries, as agents in water treatment and in appropriate pharmaceutical and cosmetic applications. The alkali metal salts, which preferably comprise sodium or potassium salts, are most conveniently prepared by the blending with propylene glycol of β-acids that have been prepared in their water-insoluble, free acid form and liquefied by heating to above about 40° C., preferably around 60° C., and the simultaneous or sequential addition of concentrated, aqueous alkali metal hydroxide solution. In this way a stable, homogeneous solution is obtained that has only a small content of water (typically about 5%). Alternatively, albeit somewhat less satisfactory methods for the preparation of such solutions include the direct dissolution of the alkali metal salts of the β-acids (prepared, for example, by the method of U.S. Pat. No. 5,624,701) or the addition of solid alkali metal hydroxide to the mixture of β-acids and propylene glycol.

BRIEF DESCRIPTION OF THE DRAWINGS

Further features and advantages of the present invention will be seen from the following detailed description, taken in conjunction with FIG. 1, which illustrates a process for production of the alkali metal salts of β-acids in propylene glycol useful in accordance with the present invention.

DETAILED DESCRIPTION OF THE INVENTION

Figure 1:
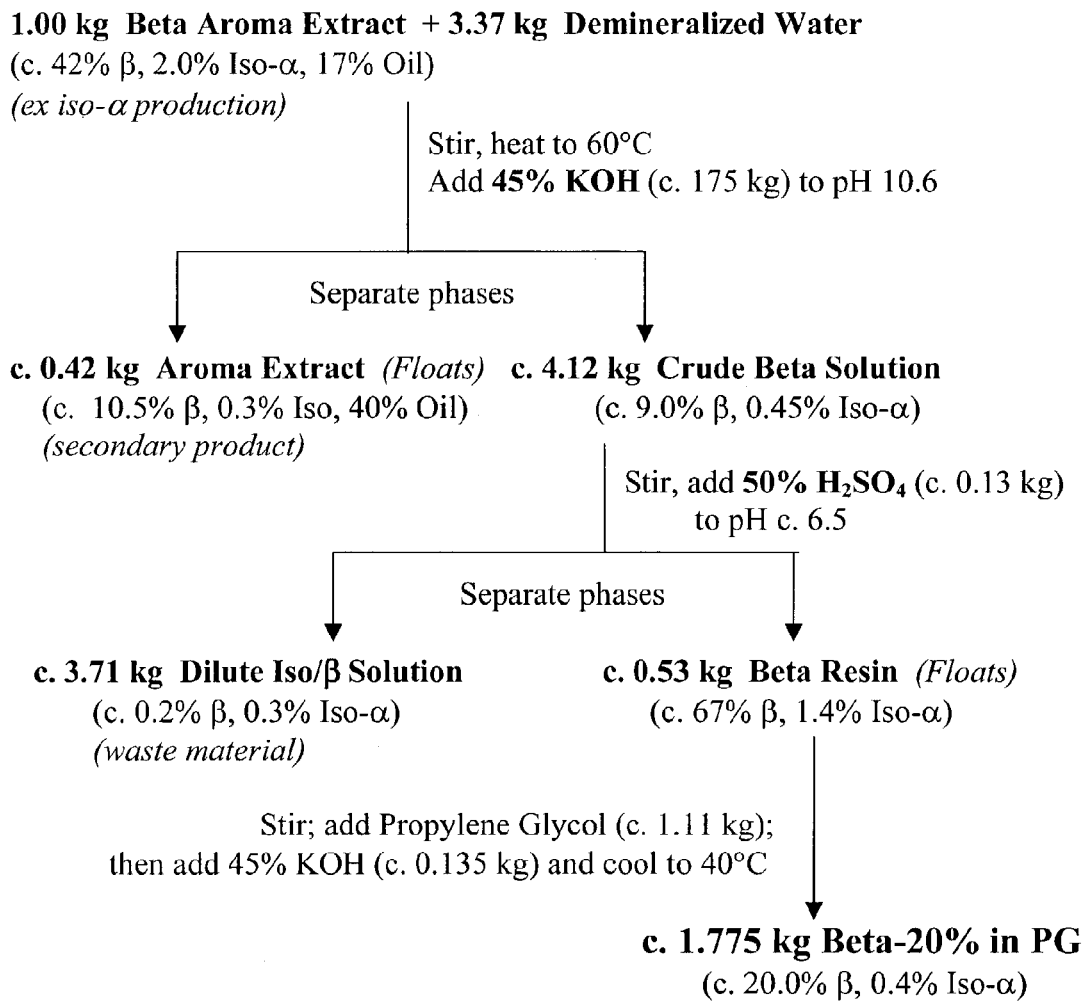

The present invention employs the alkali metal salts of β-acids in propylene glycol. Propylene glycol, which has sweet taste, potentially assists to mask any residual bitterness of the β-acids preparation arising from the presence of small amounts of the highly bitter iso-α-acids. Surprisingly, we have found that the alkali metal salts of the β-acids are more soluble in propylene glycol than are the free acids themselves, and more soluble also than they are in water. They are also remarkably stable and do not throw out any precipitates even at storage temperatures well below 0° C. These features enable more concentrated, stable and effective solutions, to be prepared, transported, stored and used than has hitherto been achieved. Conveniently, they are also miscible with water, facilitating easy dosing at reduced concentrations. Propylene glycol is therefore especially valuable in its use as a solvent or carrier for β-acids in accordance with the present invention.

The β-acids as used herein may be prepared from organic solvent extracted hops, liquid CO2 extracted hops or supercritical CO2 extracted hops. Preferred is the β-acids fraction obtained by liquid CO2 extraction of hops. β-acids extracts of hops contain three major homologs—colupulone, lupulone and adlupulone. All three homologs are believed to be active as anti-microbial agents. The β-acids in propylene glycol may be sprayed onto food materials, or the food materials dipped into a solution containing the β-acids, dosed into process streams as an anti-microbial agent or else added as ingredients in the formulation of cosmetic or pharmaceutical products.

The β-acids are typically dissolved in propylene glycol as their alkali metal salts to provide a solution containing 1–30% of β-acids, preferably about 5–25%, most preferably about 20% by weight of β-acids. Useful, stable solutions of the alkali metal salts of certain other hop resin acids may also prepared. Propylene glycol is regarded as a very safe, GRAS (generally regarded as safe) material that is widely used as a carrier for food ingredients, being generally permitted for use in foodstuffs at levels not to exceed good manufacturing practice. Under United States FDA regulations it is specifically permitted at up to 2.5% in frozen dairy products, 5% in alcohol beverages, 24% in confections and frostings, and 97% in seasonings.

A particular feature and advantage to the present invention is that propylene glycol has a sweet flavor which may be expected to partially mask the normally slightly bitter flavor of β-acids preparations when used in food processing applications.

EXAMPLES

The following Examples are intended to illustrate, but not limit, the scope of the invention.

Example 1

Process for Production of Potassium Salt form β-Acids in Propylene Glycol

This Example illustrates a process for the production of beta acids in propylene glycol.

Referring to FIG. 1, 1.00 kg of a "Beta Aroma Extract" obtained as a by-product of iso-α-acids manufacture are added to 3.365 kg of demineralized water, stirred and heated to 60° C. Concentrated potassium hydroxide (45% by weight in aqueous solution) is added to the stirred solution until a pH of about 10.6 is reached, causing the majority of the β-acids to dissolve. After stirring for several minutes, the oily (organic) and aqueous layers are allowed to separate. The aqueous layer containing the bulk of the β-acids is collected and 50% (by weight) sulfuric acid in aqueous solution added until a pH of about 6.5 is reached, the β-acids then having been mostly precipitated out of solution. After stirring for a few minutes, the organic and aqueous layers are allowed to separate. The aqueous layer is then removed. Finally, the hot, β-acids rich, mobile organic phase is added to a calculated quantity of propylene glycol, an aqueous solution of potassium hydroxide (45% w/w) sufficient to convert the β-acids into their potassium salt form is stirred in, this mixture being simultaneously cooled to 40° C. and yielding a solution of β-acids (20% w/w) in propylene glycol. Persons skilled in the art will appreciate that a purer preparation of β-acids in propylene glycol can be made by altering the conditions of the initial purification stages or by adding further aqueous extraction and separation stages to the process before the final formulation stage. Such extra purification was applied to the production of the β-acids resin used as the raw material in the next example.

Example 2

Production of Potassium Salt Form β-Acids in Propylene Glycol

A mixture of 46.35 g of a β-acids, free acid resin form preparation containing 71.7% by weight β-acids by HPLC (using ICE-2 standard) and 100.0 g of propylene glycol (USP grade) were warmed to 60° C. and blended together in a glass beaker at 500 rpm using a 6 cm diameter impeller.

Then 8.5 ml of 45% (w/w) potassium hydroxide solution was added. The resultant product was a brown, clear, slightly viscous fluid containing 19.9% by weight of β-acids (HPLC, ICE-2 standard). A 5 g aliquot of this sample was diluted with 10 ml of water and had a pH of 10.7. This sample when cooled to ambient remained translucent and remained an essentially homogeneous fluid, albeit a rather viscous one, even when subjected to chilling to about −15° C. in a freezer.

Example 3

Process for Making 15% Beta (Sodium Salt) in Propylene Glycol 33.2 g of a free-acids form β-acids preparation (67.6% beta acids by HPLC using ICE-2 standard) and 71.9 g of propylene glycol (USP grade) were warmed to 60° C. and stirred and then 3.6 ml of 50% (w/w) aqueous sodium hydroxide solution was added. A 4 g aliquot with 8 g of water had a pH of 11.1. An aliquot of this sample gellified upon cooling to ambient. A total of another 33 g of added propylene glycol was required to prevent gel formation upon cooling to ambient. This sample consisted of 14.8% β-acids (HPLC, ICE-2 standard). A 5 g aliquot diluted with 10 ml of water had a pH of 10.8.

Example 4

Comparison of Stability of 10% β-Acids in Aqueous with 20% β-Acids in Propylene Glycol To 193.6 g of "beta aroma extract" (47.1% β-acids by HPLC using ICE-2 standard) was added 550 ml of deionized water. With stirring, and at 60° C., 18.2 ml of 45% KOH was added to bring the pH to 10.3. After allowing the phases to separate for 1.5 hours in a separatory funnel held in a 60° C. oven, the lower, turbid aqueous phase was removed. After cooling to ambient, this aqueous phase was filtered through a Whatman No. 1 paper; the filtrate being transluscent and consisting of 10.7% beta-acids (w/w, by HPLC). This filtrate was allowed to stand overnight in a refrigerator at about 3° C. and more precipitate was removed by a second filtration through Whatman No. 1 paper. The filtrate was finally diluted with water to 10.1% β-acids (HPLC, ICE-2 standard) and the pH brought to 11.1 with a small amount of 45% KOH. An aliquot of this solution was stored in a PETG bottle at ambient for 6 months. The concentration of β-acids in solution had decreased to 9.0% and there was a layer of resin on bottom of the bottle. By comparison, after one year of storage at ambient in PETG bottle the 20% β-acids in propylene glycol of Example 2, had no visible resin settled out and had a concentration of β-acids of 20.2% (HPLC, ICE-2 standard); indicating no significant change in the concentration of β-acids. This example shows the superior stability of the 20% solution of β-acids in propylene glycol, whereby the undesirable precipitation of β-acids and other waxy substances that occurs over time in the 10% β-acids in water solution is completely eliminated.

Example 5

Thermal Stability of β-Acids in Propylene Glycol

A sample of the 20% β-acids (potassium salt) solution product from Example 2, was placed in a glass vial and stored at 60° C. for 4 weeks before examination and re-analysis by HPLC. The solution was found to have remained free of precipitate and the β-acids content was unchanged at 19.9%, indicating that the potassium salts form β-acids solution was stable over the period of the test.

Example 6

Anti-Bacterial Activity of Potassium Salt form β-Acids in Propylene Glycol

An aliquot of the 20% β-acids product solution of Example 2 was diluted in water to give concentrations needed to determine the minimum inhibitory amount for bacterial growth when added to inoculated trypticase soy broth. The samples at the concentrations shown in Tables 1 & 2 were tested in two separate experiments on the following Gm +ve microbes: *Bacillus subtilis, Bacillus megaterium, Staphylococcus saprophyticus* and *Streptococcus salivarius*. It may be seen that total inhibition was achieved at 10 to 100 µg/mL, depending on the particular microorganisms.

TABLE 1

Experimental test of antibacterial potency of potassium salt form β-acids in propylene glycol

| Dose Rate | Test Organism | | | |
|---|---|---|---|---|
| (µg/ml) | B. Subtilis | B. megaterium | S. saprophyticus | S. salivarius |
| 0.0 | ++++ | ++++ | ++++ | ++++ |
| 0.3 | ++++ | ++++ | +++ | ++++ |
| 1 | ++++ | ++++ | +++ | ++ |
| 3 | ++ | +/− | ++ | ++ |
| 10 | no growth | no growth | no growth | +/− |

++++ = no inhibition

TABLE 2

2$^{nd}$ experimental test of antibacterial potency of potassium salt form β-acids in propylene glycol

| Dose Rate | Test Organism | | | |
|---|---|---|---|---|
| (µg/ml) | B. Subtilis | B. megaterium | S. saprophyticus | S. salivarius |
| 0.0 | ++++ | ++++ | ++++ | ++++ |
| 0.3 | +++ | ++++ | +++ | ++++ |
| 1 | ++ | ++++ | +++ | ++++ |
| 3 | ++ | no growth | +/− | +++ |
| 10 | no growth | no growth | no growth | +/− |
| 30 | not tested | not tested | not tested | +/− |
| 100 | not tested | not tested | not tested | no growth |

++++ = no inhibition

Example 7

An aliquot of the 20% β-acids product solution of Example 2 was added to an ointment at 2 mg/g of ointment, representing an addition of 400 ppm of β-acids. After thoroughly blending the ingredients together in a mortar, inhibitory activity was determined against the organism *Bacillus subtilis* in a diffusion test, as follows:

A bacterial suspension having an inoculum density of approximately $1 \times 10^8$ CFU/ml (colony forming units per mL) was added to 10 mL of melted trypticase soy agar at 46° C. After inoculating with the test organism the agar was mixed thoroughly and then poured into a plastic petri dish.

After hardening of the agar, wells were made using a cork borer (7 mm diam.). Each well was then filled either with base ointment (control) or with the ointment containing added β-acids.

Duplicate plates were prepared and the two dishes incubated for 24 hrs at 37° C., by which time a homogeneous lawn of bacteria had developed over the surface of the agar, excepting that a clear zone could be seen around the wells that contained the test ointment. The radius of the inhibition zones was measured to the nearest 0.1 cm and each time the zone of inhibition measured 0.2 cm, demonstrating the efficacy of the small amount of β-acids that had been added to the test ointment in the form of their potassium salts solution in propylene glycol.

While the invention has been described by way of example and in terms of the preferred embodiment, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A process for the preparation of a solution of hop-derived β-acids suitable for use in the inhibition of bacterial growth and comprising the steps of:

(a) heating a mixture of β-acids and propylene glycol;
   (b) simultaneously or sequentially adding a concentrated, aqueous solution of an alkali metal hydroxide to the heated mixture sufficient to obtain a homogeneous solution having a pH of at least about 9.0 (as measured after 3x dilution into water), and
   (c) cooling said homogeneous solution.

2. The process of claim 1, wherein the alkali metal is potassium or sodium.

3. The process of claim 1, wherein the β-acids solution contains from about 1 to 30 weight percent of β-acids.

4. The process of claim 1, wherein the β-acids solution contains from about 5 to 25 weight percent of β-acids.

5. The process of claim 1, wherein the β-acids solution contains about 20 weight percent of β-acids.

6. A preparation of the alkali metal salts of hop-derived β-acids in an aqueous solution of propylene glycol prepared according to the process as claimed in claim 1 and in which the concentration of the β-acids exceeds 10 weight percent.

7. A preparation of the alkali metal salts of hop-derived β-acids in an aqueous solution of propylene glycol as claimed in claim 6, having a water content below about 7%.

* * * * *

UNITED STATES PATENT AND TRADEMARK OFFICE
CERTIFICATE OF CORRECTION

PATENT NO. : 7,361,374 B2  Page 1 of 1
APPLICATION NO. : 10/438656
DATED : April 22, 2008
INVENTOR(S) : Wilson et al.

It is certified that error appears in the above-identified patent and that said Letters Patent is hereby corrected as shown below:

Title Page item 56 insert

| Document No. | Date | Name | Classification |
|---|---|---|---|
| --US-5,082,975 | 01-1992 | Todd et al. | 568/315-- |

Signed and Sealed this

Second Day of February, 2010

David J. Kappos
*Director of the United States Patent and Trademark Office*